United States Patent [19]

Sawamura et al.

[11] 4,232,970
[45] Nov. 11, 1980

[54] APPARATUS FOR AUTOMATIC DIAGNOSIS OF CELLS

[75] Inventors: Ichiro Sawamura; Kosaku Tsuboshima, both of Hachioji, Japan

[73] Assignee: Olympus Optical Co., Ltd., Tokyo, Japan

[21] Appl. No.: 885,771

[22] Filed: Mar. 13, 1978

[30] Foreign Application Priority Data

Apr. 30, 1977 [JP] Japan ................................. 52-50559

[51] Int. Cl.$^2$ ..................... G01N 21/22; G01N 33/16; G01N 21/60
[52] U.S. Cl. .......................... 356/432; 340/146.3 CA; 356/39
[58] Field of Search .......................... 356/39, 371, 432; 340/146.3 CA; 250/461, 461 B, 201, 204; 350/46; 354/25

[56] References Cited

U.S. PATENT DOCUMENTS

| | | | |
|---|---|---|---|
| 3,349,406 | 10/1967 | Perry et al. | 250/227 |
| 3,851,972 | 12/1974 | Smith et al. | 356/39 |
| 3,857,031 | 12/1974 | Sinclair et al. | 250/201 |
| 3,967,110 | 6/1976 | Rogers et al. | 250/201 |
| 4,000,417 | 12/1976 | Adkisson et al. | 250/201 |
| 4,078,171 | 3/1978 | Stauffer | 250/201 |

FOREIGN PATENT DOCUMENTS 2308119  11/1976  France ....................................... 354/25

OTHER PUBLICATIONS

Sawamura et al., "The Present State & The Future of Automated Cytolobic Diagnosis of Uterine Cancer," The Practice of Obstetrics & Gynecology, vol. 24, #B, 12-1975, pp. 1137-1143.
Sawamura et al., "Translation of Pertinent Portions of Japanese Pub. Examined Patent Application #Sho-51/39547, 10-28-76.
Sage, B. H., "White Blood Cell Analyzer," Conf. Proc. of the 16th Annual Tech. Meeting of the Soc. of Photo-Optical Instrumentation Engineers, vol. 4, San Mateo, Calif., USA, 16-18 Oct. 72, pp. 163-173.
Rottmann, H. R., "Automatic Thin-Film Pinhole Detector," IBM Tech. Disc. Bulletin, vol. 12 #1, 6-1969, pp. 185.
Husain et al., "Automation in Cervical Cancer Screening, Part I: Fixed Cell Scanning Systems," Biomedical Engineering vol. 11, 1976, pp. 161-166.

Primary Examiner—John K. Corbin
Assistant Examiner—Wm. H. Punter
Attorney, Agent, or Firm—Weinstein & Sutton

[57] ABSTRACT

An apparatus for automatic diagnosis of cells comprises a microscope, a scanning stage on the microscope, a sample carrier used to feed a sample to the scanning stage automatically, an automatic focussing mechanism, a detector assembly for detecting the light absorbance of the sample, and computation means. The computation means controls the operation of the components mentioned and automatically performs the processing of data obtained from the detector assembly, whereby the overall operation from the supply of cells to the diagnostic determination thereof is fully automated.

4 Claims, 16 Drawing Figures

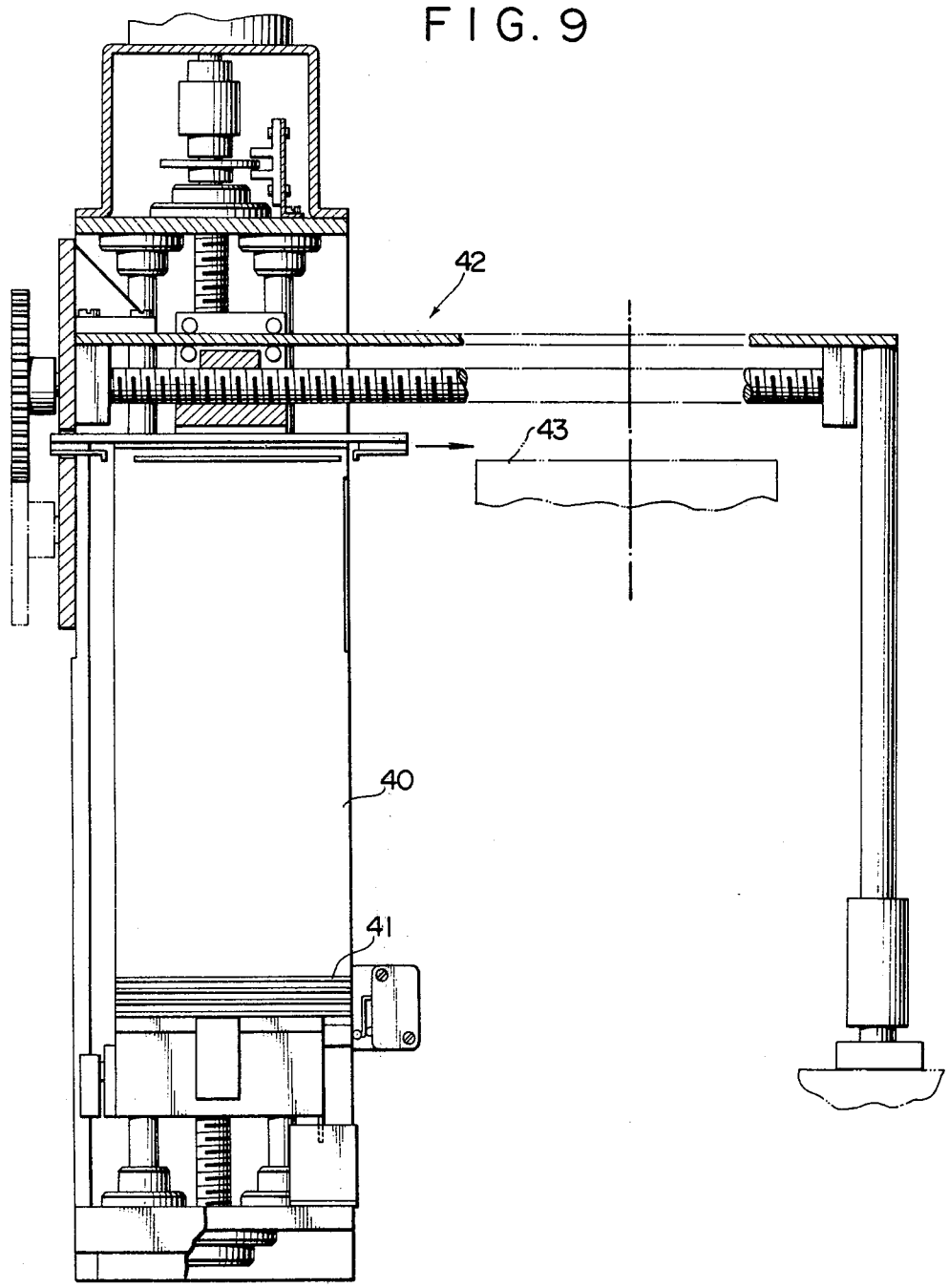

APPARATUS FOR AUTOMATIC DIAGNOSIS OF CELLS

BACKGROUND OF THE INVENTION

The invention relates to an apparatus for automatic diagnosis of cells which employs the technique of microscope spectrophotometry to examine cells for automatically determining whether the cells are affected by cancer or not.

It is possible to determine whether a substance to be examined is of an anionoid or cationoid nature from the amount of DNA (deoxyribonucleic acid) and the diameter of a cell nucleus. A scanning integration technique may be employed to obtain the amount of DNA in the cell nucleus by the microscope spectrophotometry. To accomplish this, a spot of monochromatic light is used to scan the cell nucleus in order to determine the concentration pattern of each section traversed. The amount of DNA in the cell nucleus is obtained by summing together the integral of the concentration of each section. Also, the length from the rising to the falling end of the concentration pattern of each section is determined, and the diameter of the nucleus can be determined by choosing the maximum one of these diameters. When this method of determining the cells is utilized in an apparatus for automatic diagnosis of cells which is used to process a multitude of specimens to be examined, a high speed detection, scanning and determination of the cells becomes necessary because of the necessity to accommodate the large number of specimens to be treated efficiently. However, the full extent of the applied area must be scanned, and the measured values of the respective sections of each individual cell nucleus must be related to a corresponding cell nucleus in order to determine the amount of DNA in each cell nucleus. This leads to a complicated arrangement for the resulting processing apparatus, and unless an expensive arrangement is provided, the speed of processing will be reduced.

SUMMARY OF THE INVENTION

It is an object of the invention to provide an apparatus for automatic diagnosis of cells in which a microscopic spectrophotometer is associated with an automatic sample feeder, a sample detector assembly and a data processing system, all of which are automatically controlled by calculation means to automate the entire diagnosis operation from the supply of cells to their diagnostic determination which is efficiently accomplished at high speed and in an inexpensive manner.

BRIEF DESCRIPTION OF THE DRAWINGS

FIG. 9 is an enlarged front view of a sample cassette and a sample carrier used in the apparatus of the invention;

DESCRIPTION OF PREFERRED EMBODIMENT

Figure 1:
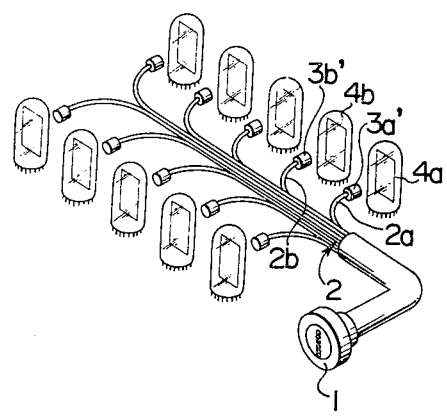
FIG. 1 is a perspective view of one embodiment of a multi-scanner employed in the present invention.
Figure 2:
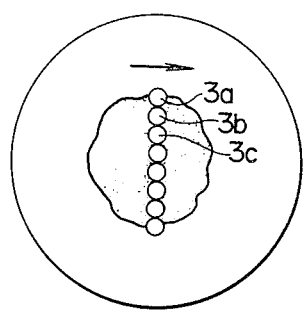
FIG. 2 is an enlarged plan view of the end face of the solid terminal of the multi-scanner of FIG. 1.
Figure 3:
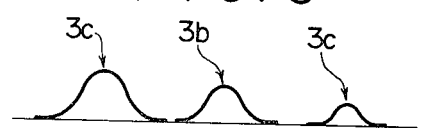
FIG. 3 graphically shows two examples of concentration patterns which may be obtained from the solid end face of the multi-scanner when it is used to scan a cell nucleus.

Referring to FIG. 1, there is shown a multi-scanner which forms part of the apparatus of the invention. Specifically, it includes a solid terminal 1, and an optical fibre bundle 2 including a plurality of individual fibres $2a$, $2b$ . . . . These fibres each have their ends $3a$, $3b$, $3c$ . . . disposed in alignment with each other as shown in FIG. 2, and are solidified at this end. The end face of the solid terminal is disposed at a position where the objective of the microscope focuses a magnified image. A plurality of light sensitive receiving elements $4a$, $4b$ . . . are each respectively disposed in opposing relationship with the other ends $3a'$, $3b'$, $3c'$ . . . of the individual optical fibres, which ends are separated from each other. When the multi-scanner is used to scan a specimen S (nucleus) as shown in FIG. 4 by moving it in a direction indicated by an arrow shown in FIG. 2, the ends $3a$, $3b$, $3c$ of corresponding fibres will sense a pattern as shown in FIG. 3.

Figure 4:
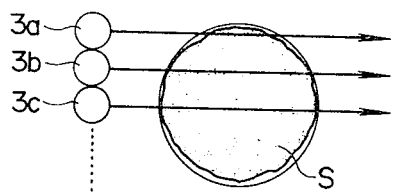
FIGS. 4, 5a–5c and 6a–6c are diagrammatic views illustrating the principle of operation of the apparatus according to the invention.
Figure 5A:
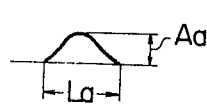
Figure 5B:
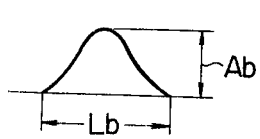
Figure 5C:
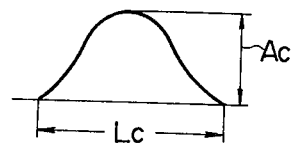
Figure 6A:
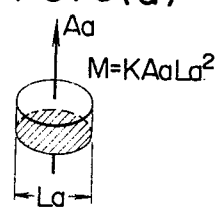
Figure 6B:
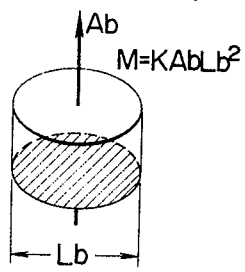
Figure 6C:
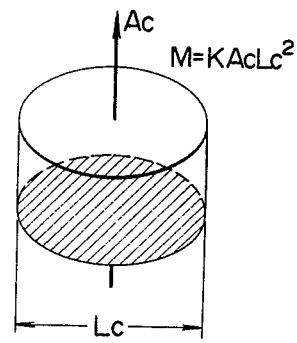

Let us assume that the specimen S shown in FIG. 4 has a cylindrical configuration which is circular in cross section and which has a given thickness. The quantity M of substance contained in the cylindrical specimen will then be given by the product of the concentration of the substance C and the volume V of the cylindrical body. The absorbance A of the substance will be represented by the product of an extinction coefficient E, the concentration C and the thickness d of the specimens. As a consequence, representing the diameter of the cylindrical body by L, the quantity M of substance contained in the specimen can be obtained as a value proportional to $AL^2$. When the solid terminal of the multi-scanner or the respective end faces $3a$, $3b$, . . . of individual fibres are moved in the direction of the arrows shown in FIG. 4 for purpose of scanning, there will be obtained concentration patterns as illustrated in FIG. 5(a), (b) and (c). The quantity of the substance in the respective sections which are scanned by the individual fibres $3a$, $3b$, $3c$ . . . can be determined, based on the absorbance of these sections, as $kA_aL_a^2$, $kA_bL_b^2$, $kA_cL_c^2$, respectively where k represents a constant, La, Lb and Lc the length of the respective sections a, b, c, or the length as measured from the rising to the falling end of the associated pattern, and Aa, Ab, Ac the maximum absorbance in the sections a, b, c. It will be noted that they correspond to the quantity of the substance contained in cylindrical bodies having respective diameters of La, Lb and Lc, as shown in FIGS. 6(a), (b) and (c), respectively. In accordance with the invention, the diagnostic determination of the cell is based on $AL^2$, using the length L of each section and the maximum absorbance A of that section, as will be further described later.

Figure 7:
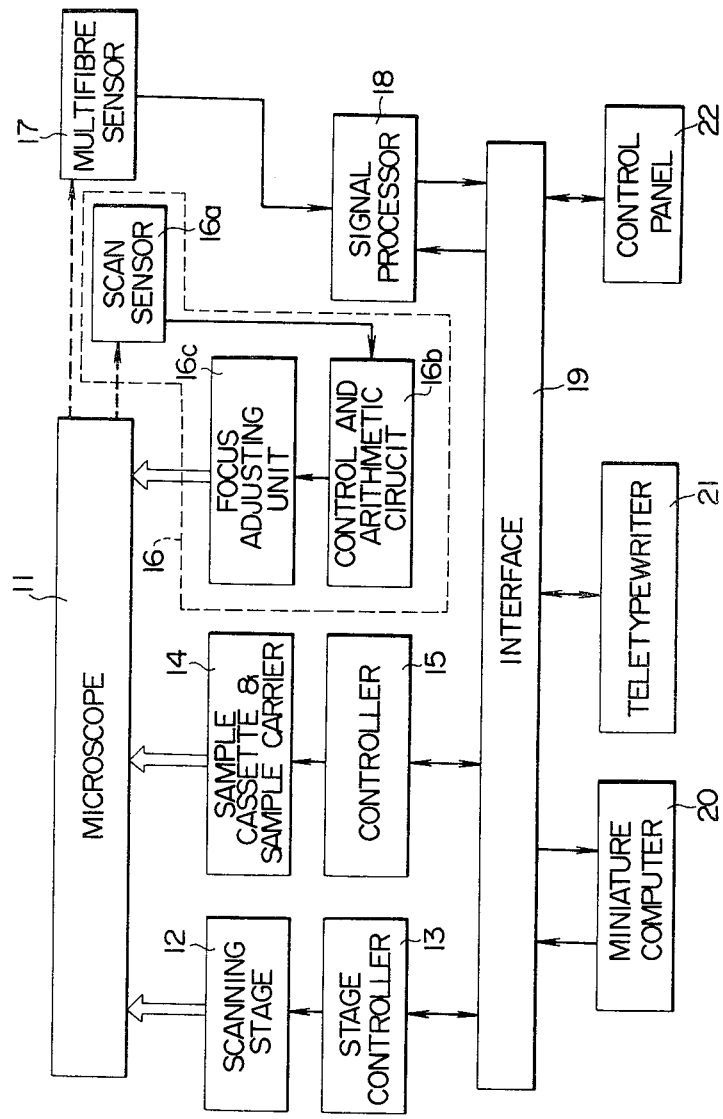
FIG. 7 is a block diagram of the apparatus of the invention.

FIG. 7 shows the general arrangement of the apparatus for automatic diagnosis of cells according to the invention. There is shown a microscope 11 of an optical system which will be described later, and the microscope is associated with a scanning stage 12, which is in turn controlled by a scanning stage controller 13. A sample cassette and sample carrier 14, constructed as described later, is also associated with the microscope 11 and is controlled by a controller 15. The microscope 11 is also associated with an automatic focussing mechanism 16, which comprises a scan sensor 16a, a focus control and arithmetic circuit 16b, and a focus adjusting unit 16c. A multiple fibre sensor 17 corresponds to the elements 4a, 4b . . . shown in FIG. 1, and is connected with a signal processor 18. The processor 18 is connected with an interface unit 19 which is in turn connected with a miniature computer 20, a teletypewriter 21 and a control panel 22.

Figure 8:
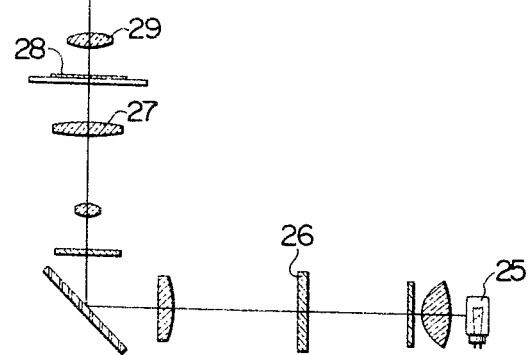
FIG. 8 is a diagrammatic view showing the optical system of the microscope used in the apparatus of the invention.

Considering these components in more detail, the microscope 11 will be initially described with reference to FIG. 8. As shown, the optical system of the microscope 11 comprises an illuminating light source 25, which may be a halogen lamp, and an interference filter 26 which is used to obtain a monochromatic light of a wavelength of 546 microns which is most strongly absorbed by the nucleus. In addition, the optical system includes a condenser lens 27, an objective 29, with a specimen 28 interposed therebetween, an eyepiece 30, a pair of semi-transmitting prisms 31, 32, and a pair of light receiving elements 33, 34 which are provided with pinholes 35, 36, respectively. A galvanometric mirror 37 is interposed between the prisms 31 and 32. In operation, light from the source 25 passes through the condenser 27 to illuminate the specimen. When illuminated, the specimen can be observed through the eyepiece 30, and an image thereof is reflected by the semi-transmitting prisms 31. The solid terminal 1 of the multi-scanner is located at the position where a magnified image of the specimen is focussed by the objective 29. The automatic focussing mechanism 16 is responsive to the light receiving elements 33, 34 which receive light passing through the pinholes 35, 36 located before and behind the imaging position of the objective 29. The elements 33, 34 and the galvanometric mirror 37 constitute together the scan sensor 16a shown in FIG. 7. The automatic focussing operation takes place by scanning the image field with the galvanometric mirror 37 and feeding the outputs of the elements 33, 34 to the arithmetic circuit 16b controlling the focus adjusting unit 16c, which effects the focussing operation. When the specimen in the microscope is exactly in focus, the degree of defocussing at the respective positions of the both pinholes will be equal to each other, so that the calculation or arithmetic circuit produces a compare output. However, if the microscope is defocussed to either side of the exact focus position, the calculated contrast value from that element which is located to the defocussed side will increase. In this instance, a stage vernier circuit is utilized to adjust the unit 16c to move the stage in the opposite direction until the outputs from the pair of elements become equal to each other. The defocussing which occurs as a result of a movement of the stage is automatically tracked within the depth of focus of the objective.

FIG. 9 shows the construction of a sample cassette and carrier. Specifically, a cassette 40 houses a plurality of samples 41, any one of which can be conveyed on a carrier 42 to the right so as to be placed on the stage 43 of the microscope, shown in phantom line. After the measurement of one sample is completed, the cassette is vertically shifted before the next sample is supplied to the stage.

Figure 10:
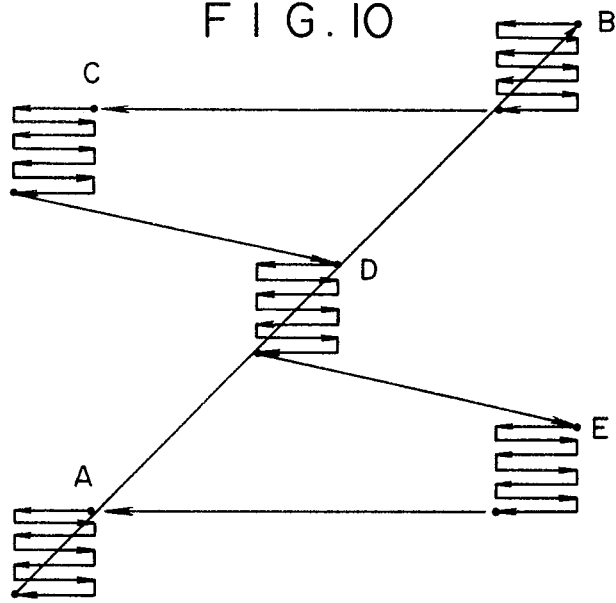
FIG. 10 is a schematic view illustrating one form of scanning of a specimen with the apparatus of the invention.

When the sample is conveyed onto the stage, the latter is moved in a manner illustrated in FIG. 10 for purposes of scanning and measuring the various parts of the sample. Specifically, when the sample is placed on a given location on the stage, it shifts from site A to site B as the stage is moved. In the meantime, the automatic focussing mechanism operates to achieve a focussing operation. Since the focussing operation is completed when the sample reaches site B, a scanning of site B takes place in the manner indicated by a sequence of arrows, determining the absorbance and the length of each cell nucleus located at such position. The scanning takes place moving the stage in the transverse direction, as viewed in FIG. 10, just in the same manner as the scanning took place in the direction indicated by the arrow of FIG. 2. Subsequently, the stage is moved in the vertical direction (relative to FIG. 10) by an amount corresponding to the length of the solid terminal of the multi-scanner, followed by a scanning in the opposite direction, and so on. Subsequently, the sample shifts from site B to site C to repeat the scanning, and thereafter shifts to site D and E in the sequential manner. Finally, the sample is returned to site A to perform the scanning spectrophotometry of the cell nucleus located in the site A, thus completing the spectrophotometry of the sample.

Figure 11:
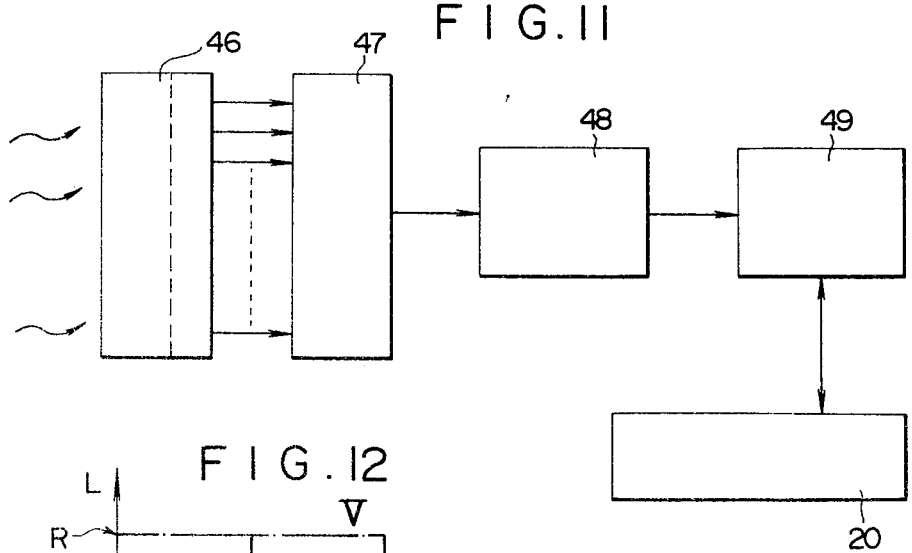
FIG. 11 is a block diagram of an output circuit which receives inputs from light receiving elements contained in the multi-scanner.

FIG. 11 shows the output circuit associated with the individual light receiving elements which are disposed in opposing relationship with the individual optical fibres. Specifically, the photometric output is fed to a preamplifier 46 having a high input impedance which compensates for variations in the transmittance from fibre bundle to fibre bundle and for differential sensitivity of the individual light receiving elements. After passing through the amplifier 46, the signal is fed to an analog multiplexer 47, which sequentially passes one channel signal to a sample-and-hold circuit 48 connected with an analog/digital converter 49. The signal is stored in the circuit 48 until it is converted into a digital signal. The converted signal is written into a memory of the miniature computer 20 while the channel separation takes place by an output pulse from the scanning stage controller 13 (FIG. 7) which is produced in proportion to the movement of the stage. The described operations, including the shifting of the stage for the purpose of scanning and transfer of the sample from the cassette to the stage, are all controlled by the miniature computer 20 as shown in FIG. 7.

Figure 12:
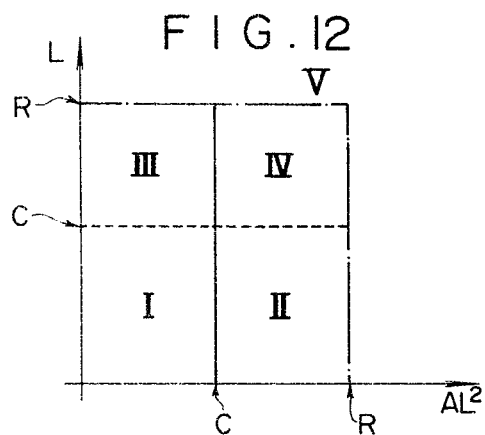
FIG. 12 is a distribution graph which shows different regions in which measurement results are sorted for purpose of diagnosis.

Data stored in the memory of the miniature computer is utilized to calculate the value of $kAL^2$ from the length L and the maximum absorbance A of each section of each cell or individual cell nuclei existing in the scanned area. The calculated values are sorted into four regions I, II, III and IV according to the values of L and $AL^2$, as shown in FIG. 12. The region I represents those cell nuclei having values L and $AL^2$ both of which are less than the threshold C. In the region II, the value of L is below the threshold while $AL^2$ is greater than the threshold. In the region III, the value of L exceeds the threshold while the value of $AL^2$ is less than the threshold. Finally, the region IV represents those cell nuclei having values of L and $AL^2$ both of which exceed the threshold. Another region V is shown for data which have values exceeding marginal values R and thus are misleading, and for which an accurate determination cannot be made. The number of samples sorted into the respective regions is determined, and their percentage with respect to the total number determined to decide whether the specimen is of either anionoid or cationoid nature. Such decision can be rendered by seeing if the number of samples contained in the region IV, for example, exceeds a given percentage which indicates an anionoid specimen. Obviously, it is desirable to determine the threshold on a statistical basis collected from a number of fundamental experiments in order to avoid an incorrect determination of the specimen. The calculated result is outputted by the teletypewriter 21 (FIG. 7), which prints out the proportion of number of samples in each of the regions with respect to the total number as well as the anionoid (+) or cationoid (−) nature of the specimen.

As described, the apparatus for automatic diagnosis cells enables a simple and a high speed processing of data obtained during the measurement since the diagnosis can be made on the basis of $kAL^2$ which is calculated by the length L and the maximum absorbance A of each section scanned of the cell being examined. The manipulation of the microscope, the supply of the sample, scanning by way of a movement of the stage, automatic focus tracking, the operation of the detector assembly and the data processing are automatically performed under the control of the computer. In this manner, the determination can be made rapidly, and the described apparatus is particularly effective to be used in the mass screening where a multitude of specimens have to be processed.

What is claimed is:

1. An apparatus for automatic diagnosis of cells wherein sequential steps from delivery of a sample to a diagnosis thereof are automatically performed, comprising:

a microscope having a displaceable scanning stage and an objective for producing an image of a sample;

a sample carrier including means for supporting a plurality of samples and means for delivering one of said samples to the scanning stage;

automatic focusing means for focusing the microscope with respect to the sample delivered to the scanning stage, said automatic focusing means comprising a scan sensor including a pair of pinholes which are separated from each other by a predetermined distance and are located before and behind the position of the image plane of said objective of said microscope, a pair of pinhole light sensitive devices for receiving light passing through said pinholes and for generating an output representative of the light received thereby, a galvanometric mirror located to reflect light received from said objective, and optical means for splitting light reflected by said galvanometric mirror so as to substantially simultaneously pass through each of said pinholes;

moving means for moving the scanning stage to scan said sample;

detector means for detecting diameter L and absorbance A of each nucleus of selected cells included in said sample as it moves relative to said detector means, said detector means comprising a plurality of optical fibres each having first and second ends, said first ends being disposed in alignment with each other and at a position where the magnified image of said sample is focused by said objective of said microscope for scanning said sample, and a light sensitive device for each of said optical fibres arranged opposite the second ends of said optical fibres for converting light detected by said light sensitive devices into an electrical signal;

processing means for processing the electrical signals developed by said detector means to calculate a value of $AL^2$ proportional to the amount of DNA included in each said nucleus of the cells selected in said sample and for generating output data representative of the processed electrical signals;

determination means responsive to said output data generated by said processing means for sorting said values of L and corresponding values proportional to $AL^2$ for each said nucleus of said cells selected in said sample into one quadrant of a system of coordinates with an axis of abscissas for L and an axis of ordinates for $AL^2$ according to whether said value L and corresponding value $AL^2$ are greater than or less than a predetermined reference value for L and $AL^2$, and for determining whether said cells are affected by cancer; and control means for controlling the operation of said sample carrier, said automatic focusing means, said moving means, said detector means, said processing means and said determination means in the proper sequence to effect automated diagnosis.

2. The apparatus of claim 1 wherein said processing means, said control means and said determination means comprise a computer.

3. The apparatus of claim 1 wherein said automatic focusing means further includes comparison means responsive to the outputs of said pinhole light sensitive devices for comparing said outputs and focus adjusting means responsive to said comparison means for moving said scanning stage so that said outputs of said pinhole light sensitive devices are equal to each other to thereby focus the microscope with respect to said sample.

4. The apparatus of claim 1 wherein said control means controls said moving means to move said scanning station in a predetermined pattern to effect the scanning of said sample, said predetermined pattern including a plurality of different scanning sites at each of which said detector means detects the size and absorbance of the section of said sample at said scanning site.

* * * * *